United States Patent [19]

Briles et al.

[11] Patent Number: 5,871,943
[45] Date of Patent: Feb. 16, 1999

[54] IMMUNOASSAY COMPRISING A TRUNCATED PNEUMOCOCCAL SURFACE PROTEIN A (PSPA)

[75] Inventors: David E. Briles; Janet L. Yother, both of Birmingham, Ala.

[73] Assignee: UAB Research Foundation, Birmingham, Ala.

[21] Appl. No.: 468,718

[22] Filed: Jun. 6, 1995

Related U.S. Application Data

[60] Continuation of Ser. No. 72,068, Jun. 3, 1993, abandoned, which is a division of Ser. No. 835,698, Feb. 12, 1992, abandoned, which is a continuation-in-part of Ser. No. 656,773, Feb. 15, 1991, abandoned.

[51] Int. Cl.$^6$ ............ G01N 33/569; G01N 33/543; C07K 14/315; C07K 17/00
[52] U.S. Cl. ............ 435/7.34; 435/7.1; 435/7.32; 435/885; 424/244.1; 424/192.1; 424/197.11; 530/350; 530/402; 530/403; 436/518; 436/524; 436/531
[58] Field of Search ............ 424/244.1, 192.1, 424/197.11; 435/7.32, 7.1, 885, 7.34; 530/350, 402, 403; 436/518, 524, 531

[56] References Cited

U.S. PATENT DOCUMENTS 4,496,538  1/1985  Gordon.
4,673,574  6/1987  Anderson.

OTHER PUBLICATIONS

Burgess et al. J. Cell Biology 111:2129–2137, Nov. 1990.
Lazar et al. Mol. Cellular Biology 8(3):1247–1252, Mar. 1988.
McDaniel et al. 1989; 89th Meeting of ASM Abstract D–255.
Yother et al. J. Bact. 17Y(2):601–609.
Dertzbaugh et al. Gene 82 (1989) 335–342.
Tizard. An Intro. Vet. Immun. 1982 pp. 120–126.
McDaniel et al (I), J. Exp. Med. 160:386–397, 1984.
McDaniel et al (II), Microbial Pathogenesis 1:519–531, 1986.
McDaniel et al (III), J. Exp. Med. 165:381–394, 1987.
McDaniel et al (IV), Infect. Immun., 59:222–228, 1991.
Crain et al, Infect. Immun., 58:3293–3299, 1990.
Abstracts of 89th Annual Meeting of the American Society for Microbiology, p. 125, item D–257, May 1989.
Abstracts of 90th Annual Meeting of the American Society for Microbiology, p. 98, item D–106, May 1990.
Abstracts of 3rd International ASM Conference on Streptococcal Genetics, p. 11, item 12, Jun. 1990.
Talkington et al, Infect. Immun. 59:1285–1289, 1991.
Yother et al, J. Bacteriol. 174:601–609, 1992; and.
Yother et al, J. Bacteriol. 174:610–618, 1992.
Growth Characteristics of Group A Streptococci in a New Chemically Defined Medium, Rijn et al—Inf. and Imm. Feb. 1980, pp. 444–448.
Young and Davis PNAS 80:1193–1198, Mar. 1983.

*Primary Examiner*—Anthony C. Caputa
*Attorney, Agent, or Firm*—Frommer Lawrence & Haug LLP; William S. Frommer; Thomas J. Kowalski

[57] ABSTRACT

A purified pneumococcal surface protein A (PspA) comprises a truncated form of the PspA protein which is immunoprotective and contains the protective epitopes of PspA. The PspA protein is soluble in physiologic solution and lacks at least the cell membrane anchor region of the whole protein. The protein is formed by insertion-duplication of mutagenesis of *S. pneumoniae* with pspA gene and expression of the truncated protein into the growth medium.

4 Claims, 8 Drawing Sheets

|  |  |  |  | a | b | c | d | e | f | g |  |
|---|---|---|---|---|---|---|---|---|---|---|---|
| GLU | GLU | ser | pro | val | ala | ser | gln | ser | LYS | ala | GLU | LYS | ASP | 14 |
|  |  |  |  |  |  |  | tyr | ASP | ala | ala | LYS | LYS | ASP | 21 |
|  |  |  |  |  |  |  | ala | LYS | asn | ala | LYS | LYS | ala | 28 |
|  |  |  |  |  |  |  | val | GLU | ASP | ala | gln | LYS | ala | 35 |
|  |  |  |  |  |  |  | leu | ASP | ASP | ala | LYS | ala | ala | 42 |
|  |  |  |  |  |  |  | gln | LYS | LYS |  |  |  |  | 45 |

| | | | | | | | | | | | | | |
|---|---|---|---|---|---|---|---|---|---|---|---|---|---|
| 1381 TCA ser | ATG met | GCG ala | ACA thr | GGA gly | TGG trp | CTC leu | CAA gln | AAC asn | AAC asn | 1411 GGT gly 1441 | TCA ser | TGG trp | TAC tyr | CTC leu | AAC asn | AGC ser | AAT asn | GGT gly |
| GCT ala 1501 | ATG met | GCT ala | ACA thr | GGT gly | TGG trp | CTC leu | CAA gln | AAC asn | AAT asn | GGT gly 1471 | TCA ser | TGG trp | TAT tyr | TAC tyr | CTC leu | AAC asn | GCT ala | AAC asn | GGC gly |
| GCT ala 1561 | ATG met | GCT ala | ACA thr | GGT gly | TGG trp | CTC leu | CAA gln | TAC tyr | AAC asn | GGT gly 1531 | TCA ser | TGG trp | TAC tyr | TAC tyr | CTC leu | AAC asn | GCT ala | AAT asn | GGT gly |
| GCT ala 1621 | ATG met | GCA ala | ACA thr | GGT gly | TGG trp | GCT ala | AAA lys | GTC val | AAC asn | GGT gly 1591 | TCA ser | TGG trp | TAT tyr | TAC tyr | CTC leu | AAC asn | GCT ala | AAC asn | GGC gly |
| GCT ala 1681 | ATG met | GCT ala | ACA thr | GGT gly | TGG trp | CTC leu | CAA gln | TAC tyr | AAC asn | GGT gly 1651 | TCA ser | TGG trp | TAT tyr | TAC tyr | CTC leu | AAC asn | GCT ala | AAT asn | GGT gly |
| GCT ala 1741 | ATG met | GCT ala | ACA thr | GGT gly | TGG trp | GCT ala | AAA lys | GTC val | AAC asn | GGT gly 1711 | TCA ser | TGG trp | TAC tyr | TAC tyr | CTC leu | AAC asn | GCT ala | AAC asn | GGT gly |
| GCT ala 1801 | ATG met | GCT ala | ACA thr | GGT gly | TGG trp | CTC leu | CAA gln | TAC tyr | AAC asn | GGT gly 1771 | TCA ser | TGG trp | TAC tyr | TAC tyr | CTC leu | AAC asn | GCT ala | AAT asn | GGT gly |
| GCT ala 1861 | ATG met | GCA ala | GCA ala | AGC ser | CAA gln | GTG val | AAA lys | GAT asp | GGA gly | GGT gly 1831 | ACC ser | TGG trp | TGG trp | TAC tyr | CTT leu | GAA glu | GCA ala | TCA ser | TTA leu |
| GCT ala 1921 | ATG met | AAA lys | GCA ala | GTC val | AAC asn | ACA thr | TTC phe | AAA lys | GTA val | GAT asp 1891 | GAT asp | AAA lys | TGG trp | TGG trp | TAT tyr | GTC val | AAT asn | AAT asn | TGG trp |
| GCC ala 1981 | GCC ala | CTT leu | GCA ala | TAA OCH | AAC asn | ACA thr | GCA ala | ACT thr | TGT cys | GAT asp 1951 | TAT tyr | AAA lys | ACA thr | GCC ala | TAA OCH | GAA glu | GGT gly | TCA ser | TTA leu |
| TAA OCH | TAA OCH | GCC ala | GCA ala | TAA OCH | ATT ile | AAA lys | GCA ala | ATG met | GGA gly | GGC gly 2011 | CAT his | TTG leu | AGG tyr | TAA OCH | TTT phe | AAT asn | GGT gly | GAA glu | TGG trp |
| AAG lys 2041 | AAG lys | CTT leu | CGA arg | TTG leu | AAT asn | AGA arg | TTT phe | ATG met | TAA OCH | GAA glu 2071 | TTC phe | TTT phe | AGG tyr | TAA OCH | TAA OCH | TTT phe | TGA OPA | AAC asn | TTA leu |
| GAT asp | | | | | | | | | | GTA val | | | TAC tyr | | | | | | AAA lys |

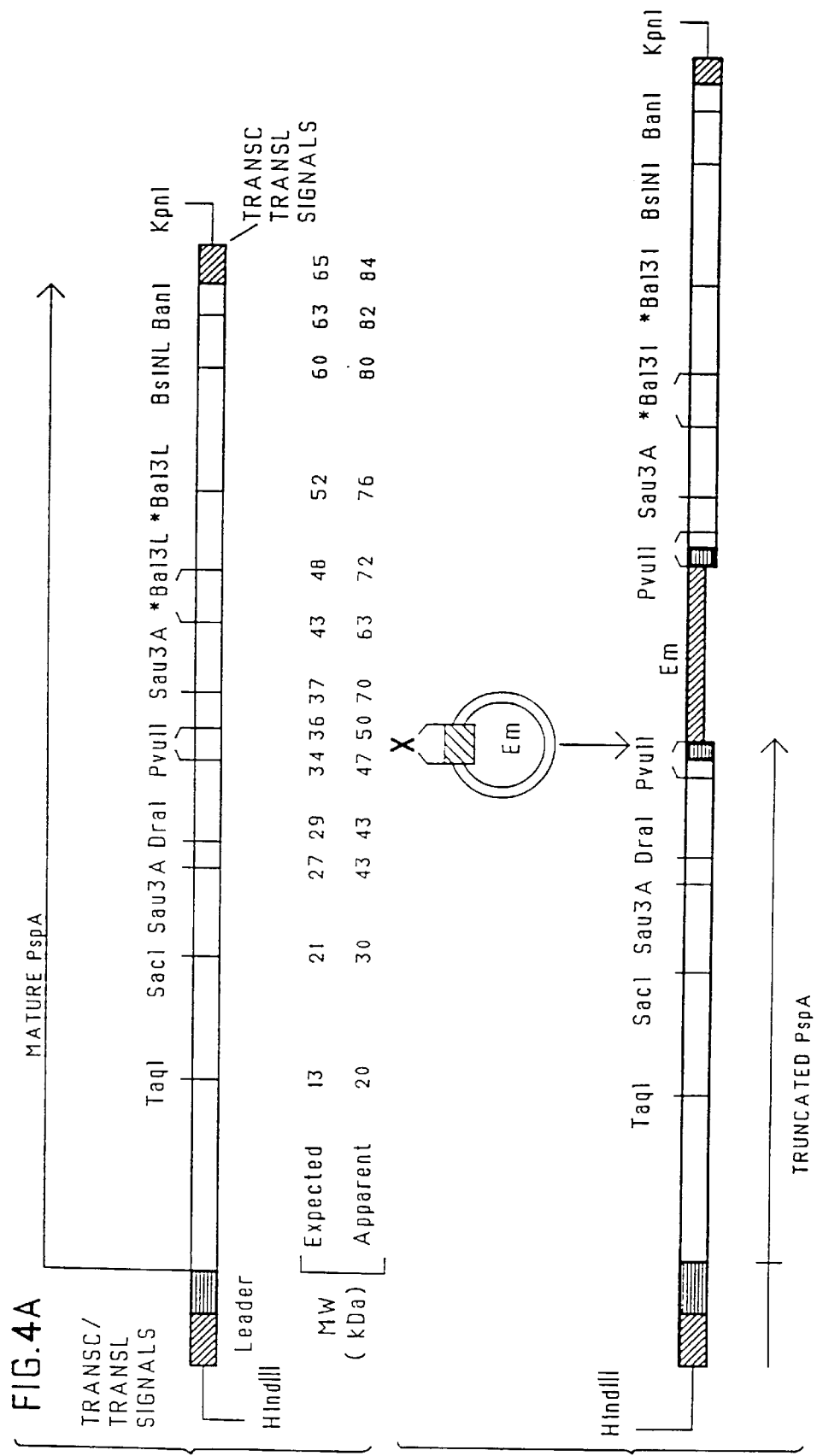

Location of epitopes detected by monoclonal antibodies to PspA

|  |  | a | b | c | d | e | f | g |
|---|---|---|---|---|---|---|---|---|
|  | 1 | E | E | s | p | v | a | s |
|  | 8 | Q | s |  |  |  |  |  |
|  |  |  |  | K | a | E | K | D |
|  | 15 | y | D | a | a | K | K | D |
|  | 22 | a | K | N | a | K | K | a |
|  | 29 | v | E | D | a | Q | K | a |
|  | 36 | L | D | D | a | K | a | a |
| X11526* | 43 | Q | K | K | y | D | E | D |
| X1126* | 50 | Q | K | K | t | E | E | K |
| X1R35 | 57 | a | a | L | E | K | a | a |
| X1R148 | 64 | s | E | E | m | D | K | a |
| X1R1224 | 71 | v | a | a | v | Q | Q | a |
|  | 78 | y | L | a | y | Q | Q | a |
|  | 85 | t | D | K | a | a | K | D |
|  | 92 | a |  |  |  |  |  |  |
|  |  |  |  |  | a | D | K | m |
|  | 97 | L | D | E | a | K | K | R |
|  | 104 | E | E | E | a | K | t | K |
|  | 111 | L | N | t | v | R | a | m |
|  | 118 | v | v | p | E | p | E | Q |
|  | 125 | L | a | E | t | K | K | K |
| 138 HHHHH | 132 | s | E | E | a | K | Q | K |
|  | 139 | a | p | E | L | t | K | K |
|  | 146 | L | E | E | a | K | a | K |
|  | 153 | L | E | E | a | E | K | K |
|  | 160 | a | t | E | a | K | Q | K |
| X1R16 | 167 | v | D |  |  |  |  |  |
|  |  |  |  | a | E | E | v | a |
|  | 174 | p | Q | a |  |  |  |  |
|  |  |  |  |  |  |  |  | K |
|  | 178 | L | a | E | L | E | N | Q |
|  | 185 | v | H | R | L | E | Q | E |
| 193 HHHHH | 192 | L | K | E | L | D | E | s |
|  | 199 | E |  |  |  |  |  |  |
|  |  |  |  |  | s | E | D | y |
|  | 204 | a | K | E | g | L | R | a |
|  | 211 | p | L | Q | s | K | L | D |
|  | 218 | a | K | K | a | K | L | s |
| X164* | 225 | K |  |  |  |  |  |  |
| X1R278* |  |  |  |  |  |  |  |  |
| X11325* | 226 | L | E | E | L | s | D | K |
|  | 233 | L | D | E | L | D | a | E |
|  | 240 | L | a | K | L | E | D | Q |
|  | 247 | L | K | a | a | E | E | N |
|  | 254 |  | N | N | v | E | D | y |
| 261 HHHHH | 260 | L | K | E | g | L | E | K |
|  | 267 | t | L | a | a | K | K | a |
| X11323* | 274 | E |  |  |  |  |  |  |
|  | 275 | L | E | K | t | E | a | D |
|  | 282 | L | K | K | a | v | N | E |

ANTIBODY REACTIVITY

| | Xi 126 | XiR 1224 | XiR 148 | XiR 1526 | XiR 35 | XiR 16 | XiR 278 | XiR 1325 | XiR 64 | XiR 1323 |
|---|---|---|---|---|---|---|---|---|---|---|
| KSD 1014 | ++ | ++ | ++ | ++ | ++ | ++ | ++ | ++ | ++ | ++ |
| JY 4306 | ++ | ++ | ++ | ++ | ++ | ++ | + | ++ | ++ | ++ |
| JY 4310 | ++ | + | ++ | ++ | ++ | ++ | – | – | – | – |
| JY 4285 | ++ | + | ++ | ++ | ++ | + | – | – | – | – |
| KSD 1500 | – | – | – | – | – | – | – | – | – | – |
| BC 100 | – | – | – | – | – | – | ++ | ++ | ++ | ++ |
| BC 207 | – | – | – | – | – | + | ++ | ++ | ++ | ++ |

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2085 base pairs
        ( B ) TYPE: nucleic acid
        ( C ) STRANDEDNESS: double
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Streptococcus pneumoniae (B) STRAIN: Rx1

(vii) IMMEDIATE SOURCE:
   (B) CLONE: JY2008

(ix) FEATURE:
   (A) NAME/KEY: intron
   (B) LOCATION: 1..2085

(ix) FEATURE:
   (A) NAME/KEY: CDS
   (B) LOCATION: join(127..1983, 1987..1992, 1996..2007, 2011
       . . 2025, 2029..2031, 2035..2085)

(xi) SEQUENCE DESCRIPTION: SEQ ID NO:1:

```
AAGCTTATGA TATAGAAATT TGTAACAAAA ATGTAATATA AAACACTTGA CAAATATTTA                60

CGGAGGAGGC TTATACTTAA TATAAGTATA GTCTGAAAAT GACTATCAGA AAAGAGGTAA               120

ATTTAG ATG AAT AAG AAA AAA ATG ATT TTA ACA AGT CTA GCC AGC GTC                  168
       Met Asn Lys Lys Lys Met Ile Leu Thr Ser Leu Ala Ser Val
         1               5                         10

GCT ATC TTA GGG GCT GGT TTT GTT GCG TCT CAG CCT ACT GTT GTA AGA                 216
Ala Ile Leu Gly Ala Gly Phe Val Ala Ser Gln Pro Thr Val Val Arg
 15              20                  25                      30

GCA GAA GAA TCT CCC GTA GCC AGT CAG TCT AAA GCT GAG AAA GAC TAT                 264
Ala Glu Glu Ser Pro Val Ala Ser Gln Ser Lys Ala Glu Lys Asp Tyr
                 35                  40                  45

GAT GCA GCG AAG AAA GAT GCT AAG AAT GCG AAA AAA GCA GTA GAA GAT                 312
Asp Ala Ala Lys Lys Asp Ala Lys Asn Ala Lys Lys Ala Val Glu Asp
             50                  55                  60

GCT CAA AAG GCT TTA GAT GAT GCA AAA GCT GCT CAG AAA AAA TAT GAC                 360
Ala Gln Lys Ala Leu Asp Asp Ala Lys Ala Ala Gln Lys Lys Tyr Asp
         65                  70                  75

GAG GAT CAG AAG AAA ACT GAG GAG AAA GCC GCG CTA GAA AAA GCA GCG                 408
Glu Asp Gln Lys Lys Thr Glu Glu Lys Ala Ala Leu Glu Lys Ala Ala
     80                  85                  90

TCT GAA GAG ATG GAT AAG GCA GTG GCA GCA GTT CAA CAA GCG TAT CTA                 456
Ser Glu Glu Met Asp Lys Ala Val Ala Ala Val Gln Gln Ala Tyr Leu
 95                 100                 105                 110

GCC TAT CAA CAA GCT ACA GAC AAA GCC GCA AAA GAC GCA GCA GAT AAG                 504
Ala Tyr Gln Gln Ala Thr Asp Lys Ala Ala Lys Asp Ala Ala Asp Lys
                115                 120                 125

ATG ATA GAT GAA GCT AAG AAA CGC GAA GAA GAG GCA AAA ACT AAA TTT                 552
Met Ile Asp Glu Ala Lys Lys Arg Glu Glu Glu Ala Lys Thr Lys Phe
            130                 135                 140

AAT ACT GTT CGA GCA ATG GTA GTT CCT GAG CCA GAG CAG TTG GCT GAG                 600
Asn Thr Val Arg Ala Met Val Val Pro Glu Pro Glu Gln Leu Ala Glu
        145                 150                 155

ACT AAG AAA AAA TCA GAA GAA GCT AAA CAA AAA GCA CCA GAA CTT ACT                 648
Thr Lys Lys Lys Ser Glu Glu Ala Lys Gln Lys Ala Pro Glu Leu Thr
    160                 165                 170

AAA AAA CTA GAA GAA GCT AAA GCA AAA TTA GAA GAG GCT GAG AAA AAA                 696
Lys Lys Leu Glu Glu Ala Lys Ala Lys Leu Glu Glu Ala Glu Lys Lys
175                 180                 185                 190

GCT ACT GAA GCC AAA CAA AAA GTG GAT GCT GAA GAA GTC GCT CCT CAA                 744
Ala Thr Glu Ala Lys Gln Lys Val Asp Ala Glu Glu Val Ala Pro Gln
                195                 200                 205

GCT AAA ATC GCT GAA TTG GAA AAT CAA GTT CAT AGA CTA GAA CAA GAG                 792
Ala Lys Ile Ala Glu Leu Glu Asn Gln Val His Arg Leu Glu Gln Glu
            210                 215                 220

CTC AAA GAG ATT GAT GAG TCT GAA TCA GAA GAT TAT GCT AAA GAA GGT                 840
Leu Lys Glu Ile Asp Glu Ser Glu Ser Glu Asp Tyr Ala Lys Glu Gly
        225                 230                 235
```

| | | | | | | | | | | | | | | | | |
|---|---|---|---|---|---|---|---|---|---|---|---|---|---|---|---|---|
| TTC | CGT | GCT | CCT | CTT | CAA | TCT | AAA | TTG | GAT | GCC | AAA | AAA | GCT | AAA | CTA | 888 |
| Phe | Arg | Ala | Pro | Leu | Gln | Ser | Lys | Leu | Asp | Ala | Lys | Lys | Ala | Lys | Leu | |
| 240 | | | | | 245 | | | | | 250 | | | | | | |
| TCA | AAA | CTT | GAA | GAG | TTA | AGT | GAT | AAG | ATT | GAT | GAG | TTA | GAC | GCT | GAA | 936 |
| Ser | Lys | Leu | Glu | Glu | Leu | Ser | Asp | Lys | Ile | Asp | Glu | Leu | Asp | Ala | Glu | |
| 255 | | | | 260 | | | | | 265 | | | | | 270 | | |
| ATT | GCA | AAA | CTT | GAA | GAT | CAA | CTT | AAA | GCT | GCT | GAA | GAA | AAC | AAT | AAT | 984 |
| Ile | Ala | Lys | Leu | Glu | Asp | Gln | Leu | Lys | Ala | Ala | Glu | Glu | Asn | Asn | Asn | |
| | | | | 275 | | | | 280 | | | | | 285 | | | |
| GTA | GAA | GAC | TAC | TTT | AAA | GAA | GGT | TTA | GAG | AAA | ACT | ATT | GCT | GCT | AAA | 1032 |
| Val | Glu | Asp | Tyr | Phe | Lys | Glu | Gly | Leu | Glu | Lys | Thr | Ile | Ala | Ala | Lys | |
| | | | 290 | | | | 295 | | | | | 300 | | | | |
| AAA | GCT | GAA | TTA | GAA | AAA | ACT | GAA | GCT | GAC | CTT | AAG | AAA | GCA | GTT | AAT | 1080 |
| Lys | Ala | Glu | Leu | Glu | Lys | Thr | Glu | Ala | Asp | Leu | Lys | Lys | Ala | Val | Asn | |
| | | 305 | | | | | 310 | | | | | 315 | | | | |
| GAG | CCA | GAA | AAA | CCA | GCT | CCA | GCT | CCA | GAA | ACT | CCA | GCC | CCA | GAA | GCA | 1128 |
| Glu | Pro | Glu | Lys | Pro | Ala | Pro | Ala | Pro | Glu | Thr | Pro | Ala | Pro | Glu | Ala | |
| 320 | | | | | 325 | | | | | 330 | | | | | | |
| CCA | GCT | GAA | CAA | CCA | AAA | CCA | GCG | CCG | GCT | CCT | CAA | CCA | GCT | CCC | GCA | 1176 |
| Pro | Ala | Glu | Gln | Pro | Lys | Pro | Ala | Pro | Ala | Pro | Gln | Pro | Ala | Pro | Ala | |
| 335 | | | | | 340 | | | | | 345 | | | | | 350 | |
| CCA | AAA | CCA | GAG | AAG | CCA | GCT | GAA | CAA | CCA | AAA | CCA | GAA | AAA | ACA | GAT | 1224 |
| Pro | Lys | Pro | Glu | Lys | Pro | Ala | Glu | Gln | Pro | Lys | Pro | Glu | Lys | Thr | Asp | |
| | | | | 355 | | | | | 360 | | | | | 365 | | |
| GAT | CAA | CAA | GCT | GAA | GAA | GAC | TAT | GCT | CGT | AGA | TCA | GAA | GAA | GAA | TAT | 1272 |
| Asp | Gln | Gln | Ala | Glu | Glu | Asp | Tyr | Ala | Arg | Arg | Ser | Glu | Glu | Glu | Tyr | |
| | | | 370 | | | | 375 | | | | | 380 | | | | |
| AAT | CGC | TTG | ACT | CAA | CAG | CAA | CCG | CCA | AAA | GCT | GAA | AAA | CCA | GCT | CCT | 1320 |
| Asn | Arg | Leu | Thr | Gln | Gln | Gln | Pro | Pro | Lys | Ala | Glu | Lys | Pro | Ala | Pro | |
| | | 385 | | | | | 390 | | | | | 395 | | | | |
| GCA | CCA | AAA | ACA | GGC | TGG | AAA | CAA | GAA | AAC | GGT | ATG | TGG | TAC | TTC | TAC | 1368 |
| Ala | Pro | Lys | Thr | Gly | Trp | Lys | Gln | Glu | Asn | Gly | Met | Trp | Tyr | Phe | Tyr | |
| | 400 | | | | | 405 | | | | | 410 | | | | | |
| AAT | ACT | GAT | GGT | TCA | ATG | GCG | ACA | GGA | TGG | CTC | CAA | AAC | AAC | GGT | TCA | 1416 |
| Asn | Thr | Asp | Gly | Ser | Met | Ala | Thr | Gly | Trp | Leu | Gln | Asn | Asn | Gly | Ser | |
| 415 | | | | | 420 | | | | | 425 | | | | | 430 | |
| TGG | TAC | TAC | CTC | AAC | AGC | AAT | GGT | GCT | ATG | GCT | ACA | GGT | TGG | CTC | CAA | 1464 |
| Trp | Tyr | Tyr | Leu | Asn | Ser | Asn | Gly | Ala | Met | Ala | Thr | Gly | Trp | Leu | Gln | |
| | | | | 435 | | | | 440 | | | | | 445 | | | |
| TAC | AAT | GGT | TCA | TGG | TAT | TAC | CTC | AAC | GCT | AAC | GGC | GCT | ATG | GCA | ACA | 1512 |
| Tyr | Asn | Gly | Ser | Trp | Tyr | Tyr | Leu | Asn | Ala | Asn | Gly | Ala | Met | Ala | Thr | |
| | | | 450 | | | | | 455 | | | | | 460 | | | |
| GGT | TGG | GCT | AAA | GTC | AAC | GGT | TCA | TGG | TAC | TAC | CTC | AAC | GCT | AAT | GGT | 1560 |
| Gly | Trp | Ala | Lys | Val | Asn | Gly | Ser | Trp | Tyr | Tyr | Leu | Asn | Ala | Asn | Gly | |
| | | 465 | | | | | 470 | | | | | 475 | | | | |
| GCT | ATG | GCT | ACA | GGT | TGG | CTC | CAA | TAC | AAC | GGT | TCA | TGG | TAT | TAC | CTC | 1608 |
| Ala | Met | Ala | Thr | Gly | Trp | Leu | Gln | Tyr | Asn | Gly | Ser | Trp | Tyr | Tyr | Leu | |
| | 480 | | | | | 485 | | | | | 490 | | | | | |
| AAC | GCT | AAC | GGC | GCT | ATG | GCA | ACA | GGT | TGG | GCT | AAA | GTC | AAC | GGT | TCA | 1656 |
| Asn | Ala | Asn | Gly | Ala | Met | Ala | Thr | Gly | Trp | Ala | Lys | Val | Asn | Gly | Ser | |
| 495 | | | | | 500 | | | | | 505 | | | | | 510 | |
| TGG | TAC | TAC | CTC | AAC | GCT | AAT | GGT | GCT | ATG | GCT | ACA | GGT | TGG | CTC | CAA | 1704 |
| Trp | Tyr | Tyr | Leu | Asn | Ala | Asn | Gly | Ala | Met | Ala | Thr | Gly | Trp | Leu | Gln | |
| | | | | 515 | | | | 520 | | | | | 525 | | | |
| TAC | AAC | GGT | TCA | TGG | TAC | TAC | CTC | AAC | GCT | AAC | GGT | GCT | ATG | GCT | ACA | 1752 |
| Tyr | Asn | Gly | Ser | Trp | Tyr | Tyr | Leu | Asn | Ala | Asn | Gly | Ala | Met | Ala | Thr | |
| | | | 530 | | | | | 535 | | | | | 540 | | | |
| GGT | TGG | GCT | AAA | GTC | AAC | GGT | TCA | TGG | TAC | TAC | CTC | AAC | GCT | AAT | GGT | 1800 |
| Gly | Trp | Ala | Lys | Val | Asn | Gly | Ser | Trp | Tyr | Tyr | Leu | Asn | Ala | Asn | Gly | |
| | | 545 | | | | | 550 | | | | | 555 | | | | |

| | | | | | | | | | | | | | | | | |
|---|---|---|---|---|---|---|---|---|---|---|---|---|---|---|---|---|
| GCT | ATG | GCA | ACA | GGT | TGG | GTG | AAA | GAT | GGA | GAT | ACC | TGG | TAC | TAT | CTT | 1848 |
| Ala | Met | Ala | Thr | Gly | Trp | Val | Lys | Asp | Gly | Asp | Thr | Trp | Tyr | Tyr | Leu | |
| | 560 | | | | 565 | | | | | 570 | | | | | | |
| GAA | GCA | TCA | GGT | GCT | ATG | AAA | GCA | AGC | CAA | TGG | TTC | AAA | GTA | TCA | GAT | 1896 |
| Glu | Ala | Ser | Gly | Ala | Met | Lys | Ala | Ser | Gln | Trp | Phe | Lys | Val | Ser | Asp | |
| 575 | | | | 580 | | | | | 585 | | | | | 590 | | |
| AAA | TGG | TAC | TAT | GTC | AAT | GGT | TTA | GGT | GCC | CTT | GCA | GTC | AAC | ACA | ACT | 1944 |
| Lys | Trp | Tyr | Tyr | Val | Asn | Gly | Leu | Gly | Ala | Leu | Ala | Val | Asn | Thr | Thr | |
| | | | | 595 | | | | 600 | | | | | 605 | | | |
| GTA | GAT | GGC | TAT | AAA | GTC | AAT | GCC | AAT | GGT | GAA | TGG | GTT | TAA | GCC | GAT | 1992 |
| Val | Asp | Gly | Tyr | Lys | Val | Asn | Ala | Asn | Gly | Glu | Trp | Val | | Ala | Asp | |
| | | | 610 | | | | 615 | | | | | | | 620 | | |
| TAA | ATT | AAA | GCA | TGT | TAA | GAA | CAT | TTG | ACA | TTT | TAA | TTT | TGA | AAC | AAA | 2040 |
| | Ile | Lys | Ala | Cys | | Glu | His | Leu | Thr | Phe | | Phe | | Asn | Lys | |
| | | | | 625 | | | | | 630 | | | | | | | |
| GAT | AAG | GTT | CGA | TTG | AAT | AGA | TTT | ATG | TTC | GTA | TTC | TTT | AGG | TAC | | 2085 |
| Asp | Lys | Val | Arg | Leu | Asn | Arg | Phe | Met | Phe | Val | Phe | Phe | Arg | Tyr | | |
| | 635 | | | | | 640 | | | | 645 | | | | | | |

(2) INFORMATION FOR SEQ ID NO:2:

(i) SEQUENCE CHARACTERISTICS:
        (A) LENGTH: 648 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met | Asn | Lys | Lys | Lys | Met | Ile | Leu | Thr | Ser | Leu | Ala | Ser | Val | Ala | Ile |
| 1 | | | | 5 | | | | | 10 | | | | | 15 | |
| Leu | Gly | Ala | Gly | Phe | Val | Ala | Ser | Gln | Pro | Thr | Val | Val | Arg | Ala | Glu |
| | | | 20 | | | | | 25 | | | | | 30 | | |
| Glu | Ser | Pro | Val | Ala | Ser | Gln | Ser | Lys | Ala | Glu | Lys | Asp | Tyr | Asp | Ala |
| | | 35 | | | | | 40 | | | | | 45 | | | |
| Ala | Lys | Lys | Asp | Ala | Lys | Asn | Ala | Lys | Lys | Ala | Val | Glu | Asp | Ala | Gln |
| | 50 | | | | | 55 | | | | | 60 | | | | |
| Lys | Ala | Leu | Asp | Asp | Ala | Lys | Ala | Ala | Gln | Lys | Lys | Tyr | Asp | Glu | Asp |
| 65 | | | | | 70 | | | | | 75 | | | | | 80 |
| Gln | Lys | Lys | Thr | Glu | Glu | Lys | Ala | Ala | Leu | Glu | Lys | Ala | Ala | Ser | Glu |
| | | | | 85 | | | | | 90 | | | | | 95 | |
| Glu | Met | Asp | Lys | Ala | Val | Ala | Ala | Val | Gln | Gln | Ala | Tyr | Leu | Ala | Tyr |
| | | | 100 | | | | | 105 | | | | | 110 | | |
| Gln | Gln | Ala | Thr | Asp | Lys | Ala | Ala | Lys | Asp | Ala | Ala | Asp | Lys | Met | Ile |
| | | 115 | | | | | 120 | | | | | 125 | | | |
| Asp | Glu | Ala | Lys | Lys | Arg | Glu | Glu | Ala | Lys | Thr | Lys | Phe | Asn | Thr | |
| | 130 | | | | | 135 | | | | | 140 | | | | |
| Val | Arg | Ala | Met | Val | Val | Pro | Glu | Pro | Gln | Leu | Ala | Glu | Thr | Lys | |
| 145 | | | | | 150 | | | | | 155 | | | | | 160 |
| Lys | Lys | Ser | Glu | Glu | Ala | Lys | Gln | Lys | Ala | Pro | Glu | Leu | Thr | Lys | Lys |
| | | | | 165 | | | | | 170 | | | | | 175 | |
| Leu | Glu | Glu | Ala | Lys | Ala | Lys | Leu | Glu | Glu | Ala | Lys | Lys | Lys | Ala | Thr |
| | | | 180 | | | | | 185 | | | | | 190 | | |
| Glu | Ala | Lys | Gln | Lys | Val | Asp | Ala | Glu | Glu | Val | Ala | Pro | Gln | Ala | Lys |
| | | 195 | | | | | 200 | | | | | 205 | | | |
| Ile | Ala | Glu | Leu | Glu | Asn | Gln | Val | His | Arg | Leu | Glu | Gln | Glu | Leu | Lys |
| | 210 | | | | | 215 | | | | | 220 | | | | |
| Glu | Ile | Asp | Glu | Ser | Glu | Ser | Glu | Asp | Tyr | Ala | Lys | Glu | Gly | Phe | Arg |
| 225 | | | | | 230 | | | | | 235 | | | | | 240 |

```
Ala  Pro  Leu  Gln  Ser  Lys  Leu  Asp  Ala  Lys  Ala  Lys  Leu  Ser  Lys
               245                250                255

Leu  Glu  Glu  Leu  Ser  Asp  Lys  Ile  Asp  Glu  Leu  Asp  Ala  Glu  Ile  Ala
          260                265                270

Lys  Leu  Glu  Asp  Gln  Leu  Lys  Ala  Ala  Glu  Glu  Asn  Asn  Val  Glu
          275                280                285

Asp  Tyr  Phe  Lys  Glu  Gly  Leu  Glu  Lys  Thr  Ile  Ala  Ala  Lys  Lys  Ala
     290                295                300

Glu  Leu  Glu  Lys  Thr  Glu  Ala  Asp  Leu  Lys  Lys  Ala  Val  Asn  Glu  Pro
305                 310                315                320

Glu  Lys  Pro  Ala  Pro  Ala  Pro  Glu  Thr  Pro  Ala  Pro  Glu  Ala  Pro  Ala
               325                330                335

Glu  Gln  Pro  Lys  Pro  Ala  Pro  Ala  Pro  Gln  Pro  Ala  Pro  Ala  Pro  Lys
               340                345                350

Pro  Glu  Lys  Pro  Ala  Glu  Gln  Pro  Lys  Pro  Glu  Lys  Thr  Asp  Asp  Gln
          355                360                365

Gln  Ala  Glu  Glu  Asp  Tyr  Ala  Arg  Arg  Ser  Glu  Glu  Tyr  Asn  Arg
     370                375                380

Leu  Thr  Gln  Gln  Gln  Pro  Pro  Lys  Ala  Glu  Lys  Pro  Ala  Pro  Ala  Pro
385                 390                395                400

Lys  Thr  Gly  Trp  Lys  Gln  Glu  Asn  Gly  Met  Trp  Tyr  Phe  Tyr  Asn  Thr
               405                410                415

Asp  Gly  Ser  Met  Ala  Thr  Gly  Trp  Leu  Gln  Asn  Asn  Gly  Ser  Trp  Tyr
               420                425                430

Tyr  Leu  Asn  Ser  Asn  Gly  Ala  Met  Ala  Thr  Gly  Trp  Leu  Gln  Tyr  Asn
          435                440                445

Gly  Ser  Trp  Tyr  Tyr  Leu  Asn  Ala  Asn  Gly  Ala  Met  Ala  Thr  Gly  Trp
     450                455                460

Ala  Lys  Val  Asn  Gly  Ser  Trp  Tyr  Tyr  Leu  Asn  Ala  Asn  Gly  Ala  Met
465                 470                475                480

Ala  Thr  Gly  Trp  Leu  Gln  Tyr  Asn  Gly  Ser  Trp  Tyr  Tyr  Leu  Asn  Ala
               485                490                495

Asn  Gly  Ala  Met  Ala  Thr  Gly  Trp  Ala  Lys  Val  Asn  Gly  Ser  Trp  Tyr
               500                505                510

Tyr  Leu  Asn  Ala  Asn  Gly  Ala  Met  Ala  Thr  Gly  Trp  Leu  Gln  Tyr  Asn
          515                520                525

Gly  Ser  Trp  Tyr  Tyr  Leu  Asn  Ala  Asn  Gly  Ala  Met  Ala  Thr  Gly  Trp
     530                535                540

Ala  Lys  Val  Asn  Gly  Ser  Trp  Tyr  Tyr  Leu  Asn  Ala  Asn  Gly  Ala  Met
545                 550                555                560

Ala  Thr  Gly  Trp  Val  Lys  Asp  Gly  Asp  Thr  Trp  Tyr  Tyr  Leu  Glu  Ala
               565                570                575

Ser  Gly  Ala  Met  Lys  Ala  Ser  Gln  Trp  Phe  Lys  Val  Ser  Asp  Lys  Trp
               580                585                590

Tyr  Tyr  Val  Asn  Gly  Leu  Gly  Ala  Leu  Ala  Val  Asn  Thr  Thr  Val  Asp
          595                600                605

Gly  Tyr  Lys  Val  Asn  Ala  Asn  Gly  Glu  Trp  Val  Ala  Asp  Ile  Lys  Ala
     610                615                620

Cys  Glu  His  Leu  Thr  Phe  Phe  Asn  Lys  Asp  Lys  Val  Arg  Leu  Asn  Arg
625                 630                635                640

Phe  Met  Phe  Val  Phe  Phe  Arg  Tyr
               645
```

( 2 ) INFORMATION FOR SEQ ID NO:3:

( i ) SEQUENCE CHARACTERISTICS:
        ( A ) LENGTH: 45 amino acids
        ( B ) TYPE: amino acid
        ( D ) TOPOLOGY: linear ( x i ) SEQUENCE DESCRIPTION: SEQ ID NO:3:

```
Glu Glu Ser Pro Val Ala Ser Gln Ser Lys Ala Glu Lys Asp Tyr Asp
 1               5                  10                  15

Ala Ala Lys Lys Asp Ala Lys Asn Ala Lys Lys Ala Val Glu Asp Ala
                20                  25                  30

Gln Lys Ala Leu Asp Asp Ala Lys Ala Ala Gln Lys Lys
                35                  40                  45
```

( 2 ) INFORMATION FOR SEQ ID NO:4:

( i ) SEQUENCE CHARACTERISTICS:
        ( A ) LENGTH: 289 amino acids
        ( B ) TYPE: amino acid
        ( C ) STRANDEDNESS: single
        ( D ) TOPOLOGY: linear ( v ) FRAGMENT TYPE: N-terminal ( x i ) SEQUENCE DESCRIPTION: SEQ ID NO:4:

```
Glu Glu Ser Pro Val Ala Ser Gln Ser Lys Ala Glu Lys Asp Tyr Asp
 1               5                  10                  15

Ala Ala Lys Lys Asp Ala Lys Asn Ala Lys Lys Ala Val Glu Asp Ala
                20                  25                  30

Gln Lys Ala Leu Asp Asp Ala Lys Ala Ala Gln Lys Lys Tyr Asp Glu
                35                  40                  45

Asp Gln Lys Lys Thr Glu Glu Lys Ala Ala Leu Glu Lys Ala Ala Ser
 50                  55                  60

Glu Glu Met Asp Lys Ala Val Ala Ala Val Gln Gln Ala Tyr Leu Ala
 65                  70                  75                  80

Tyr Gln Gln Ala Thr Asp Lys Ala Ala Lys Asp Ala Ala Asp Lys Met
                85                  90                  95

Ile Asp Glu Ala Lys Lys Arg Glu Glu Glu Ala Lys Thr Lys Phe Asn
                100                 105                 110

Thr Val Arg Ala Met Val Val Pro Glu Pro Glu Gln Leu Ala Glu Thr
                115                 120                 125

Lys Lys Lys Ser Glu Glu Ala Lys Gln Lys Ala Pro Glu Leu Thr Lys
 130                 135                 140

Lys Leu Glu Glu Ala Lys Ala Lys Leu Glu Glu Ala Glu Lys Lys Ala
 145                 150                 155                 160

Thr Glu Ala Lys Gln Lys Val Asp Ala Glu Glu Val Ala Pro Gln Ala
                165                 170                 175

Lys Ile Ala Glu Leu Glu Asn Gln Val His Arg Leu Glu Gln Glu Leu
                180                 185                 190

Lys Glu Ile Asp Glu Ser Glu Ser Glu Glu Asp Tyr Ala Lys Glu Gly
                195                 200                 205

Phe Arg Ala Pro Leu Gln Ser Lys Leu Asp Ala Lys Lys Ala Lys Leu
                210                 215                 220

Ser Lys Leu Glu Glu Leu Ser Asp Lys Ile Asp Glu Leu Asp Ala Glu
 225                 230                 235                 240

Ile Ala Lys Leu Glu Asp Gln Leu Lys Ala Ala Glu Glu Asn Asn Asn
                245                 250                 255

Val Glu Asp Tyr Phe Lys Glu Gly Leu Glu Lys Thr Ile Ala Ala Lys
```

-continued

| | | | | | | | | | | | | | | |
|---|---|---|---|---|---|---|---|---|---|---|---|---|---|---|
| | | | 260 | | | | | 265 | | | | | 270 | |
| Lys | Ala | Glu | Leu | Glu | Lys | Thr | Glu | Ala | Asp | Leu | Lys | Lys | Ala | Val | Asn |
| | | 275 | | | | | 280 | | | | | 285 | | | |
| Glu | | | | | | | | | | | | | | | |

(2) INFORMATION FOR SEQ ID NO:5:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

CCGGATCCAG CTCCTGCACC AAAAAC 26

(2) INFORMATION FOR SEQ ID NO:6:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

GCGCTGCGAC GGCTTAAACC CATTCACCAT TGG 33

IMMUNOASSAY COMPRISING A TRUNCATED PNEUMOCOCCAL SURFACE PROTEIN A (PSPA)

REFERENCE TO RELATED APPLICATION

This application if a continuation of application Ser. No. 08/072,068, filed Jun. 3, 1993, now abandoned, which is a divisional of application Ser. No. 07/835,698, filed Feb. 12, 1992, now abandoned which is a continuation-in-part of application Ser. No. 07/656,773 filed Feb. 15, 1991, now abandoned.

FIELD OF INVENTION

The present invention is concerned with the development of an improved vaccine against pneumococcal infections.

BACKGROUND TO THE INVENTION

*Streptococcus pneumoniae* is an important cause of otitis media, meningitis, bacteremia and pneumonia. Despite the use of antibiotics and vaccines, the prevalence of pneumococcal infections has declined little over the last twenty-five years.

It is generally accepted that immunity to *Streptococcus pneumoniae* can be mediated by specific antibodies against the polysaccharide capsule of the pneumococcal. However, neonates and young children fail to make an immune response against polysaccharide antigens and can have repeated infections involving the same capsular serotype.

One approach to immunizing infants against a number of encapsulated bacteria is to conjugate the capsular polysaccharide antigens to protein to make them immunogenic. This approach has been successful, for example, with *Haemophilus influenzae b* (see U.S. Pat. No. 4,496,538 to Gordon and U.S. Pat. No. 4,673,574 to Anderson). However, there are over eighty known capsular serotypes of *S. pneumoniae* of which twenty-three account for most of the disease. For a pneumococcal polysaccharide-protein conjugate to be successful, the capsular types responsible for most pneumococcal infections would have to be made adequately immunogenic. This approach may be difficult, because the twenty-three polysaccharides included in the presently-available vaccine are not all adequately immunogenic, even in adults.

An alternative approach for protecting children, and also the elderly, from pneumococcal infection would be to identify protein antigens that could elicit protective immune responses. Such proteins may serve as a vaccine by themselves, may be used in conjunction with successful polysaccharide-protein conjugates, or as carriers for polysaccharides.

In McDaniel et al (I), J. Exp. Med. 160:386–397, 1984, there is described the production of hybridoma antibodies that recognize cell surface polypeptide(s) on *S. pneumoniae* and protection of mice from infection with certain strains of encapsulated *pneumococci* by such antibodies. This surface protein antigen has been termed "pneumococcal surface protein A" or PspA for short.

In McDaniel et al (II), Microbial Pathogenesis 1:519–531, 1986, there are described studies on the characterization of the PspA. Considerable diversity in the PspA molecule in different strains was found, as were differences in the epitopes recognized by different antibodies.

In McDaniel et al (III), J. Exp. Med. 165:381–394, 1987, there is disclosed that immunization of X-linked immunodeficient (XID) mice with non-encapsulated *pneumococci* expressing PspA, but not isogenic *pneumococci* lacking PspA, protects mice from subsequent fatal infection with *pneumococci*.

In McDaniel et al (IV), Infect. Immun., 59:222–228, 1991, there is described immunization of mice with a recombinant full length fragment of PspA that is able to elicit protection against pneumococcal strains of capsular types 6A and 3.

In Crain et al, Infect. Immun., 56:3293–3299, 1990, there is described a rabbit antiserum that detects PspA in 100% (n=95) of clinical and laboratory isolates of strains of *S. pneumoniae*. When reacted with seven monoclonal antibodies to PspA, fifty-seven *S. pneumoniae* isolates exhibited thirty-one different patterns of reactivity.

The PspA protein type is independent of capsular type. It would seem that genetic mutation or exchange in the environment has allowed for the development of a large pool of strains which are highly diverse with respect to capsule, PspA, and possibly other molecules with variable structures. Variability of PspA's from different strains also is evident in their molecular weights, which range from 67 to 99 kD. The observed differences are stably inherited and are not the result of protein degradation.

Immunization with a partially purified PspA from a recombinant 1 gt11 clone, elicited protection against challenge with several *S. pneumoniae* strains representing different capsular and PspA types, as described in McDaniel et al (IV), Infect. Immun. 59:222–228, 1991. Although clones expressing PspA were constructed according to that paper, the product was insoluble and isolation from cell fragments following lysis was not possible.

While the protein is variable in structure between different pneumococcal strains, numerous cross-reactions exist between all PspA's, suggesting that sufficient common epitopes may be present to allow a single PspA or at least a small number of PspA's to elicit protection against a large number of *S. pneumoniae* strains.

In addition to the published literature specifically referred to above, the inventors, in conjunction with co-workers, have published further details concerning PspA's, as follows:

1. Abstracts of 89th Annual Meeting of the American Society for Microbiology, p. 125, item D-257, May 1989;
2. Abstracts of 90th Annual Meeting of the American Society for Microbiology, p. 98, item D-106, May 1990;
3. Abstracts of 3rd International ASM Conference on Streptococcal Genetics, p. 11, item 12, June 1990;
4. Talkington et al, Infect. Immun. 59:1285–1289, 1991;
5. Yother et al, J. Bacteriol. 174:601–609, 1992; and
6. Yother et al, J. Bacteriol. 174:610–618, 1992.

The latter three publications occurred after the filing of the aforesaid U.S. Ser. No. 07/656,773, now abandoned.

In the specification which follows and the drawings accompanying the same, there are utilized certain accepted abbreviations with respect to the amino acids represented thereby. The following Table I identifies those abbreviations:

TABLE I

| AMINO ACID ABBREVIATIONS | |
|---|---|
| A = Ala = Alanine | M = Met = Methionione |
| C = Cys = Cysteine | N = Asn = Asparagine |
| D = Asp = Aspartic Acid | P = Pro = Proline |
| E = Glu = Glutamic Acid | Q = Gln = Glutamine |
| F = Phe = Phenylalanine | R = Arg = Arginine |

TABLE I-continued

AMINO ACID ABBREVIATIONS

| G = Gly = Glycine | S = Ser = Serine |
|---|---|
| H = His = Histidine | T = Thr = Threonine |
| I = Ile = Isoleucine | V = Val = Valine |
| K = Lys = Lysine | W = Try = Tryptophan |
| L = Leu = Leucine | Y = Tyr = Tyrosine |

SUMMARY OF INVENTION

The present invention relates to the preparation of mutants of S. pneumoniae that secrete an immunogenic truncated form of the PspA protein, and isolation and purification of the secreted protein. The truncated form of the PspA protein is immunoprotective and contains the protective epitopes of PspA. The PspA protein is soluble in physiologic solution and lacking at least the functional cell membrane anchor region.

BRIEF DESCRIPTION OF DRAWINGS

FIGS. 3A–C is the DNA sequence of the pspA gene (see SEQ ID No. 1) with deduced amino acid sequence for the PspA (see SEQ ID No. 2) protein;

FIGS. 4A–B depicts the restriction map of pspA (FIG. 4A) and the use of insertion-duplication mutagenesis to construct mutations in the pspA gene (FIG. 4B), FIG. 5 shows the deduced amino acid sequence for the N-terminal region of PspA (see SEQ ID No. 4) and the general location of epitopes recognized by monoclonal antibodies;

FIG. 6 shows antibody reactivity with PspA fragments produced by various pspA gene segments.

GENERAL DESCRIPTION OF INVENTION

According to one aspect of the present invention, there is provided a purified immunoprotective pneumococcal surface protein, comprising a truncated form of PspA which contains the immunoprotective epitopes of the protein and up to about 90% of the whole PspA protein and from which the functional cell membrane anchor region is absent.

Through the technique of insertion-duplication mutagenesis of the pspA gene of the strain Rx1 of Streptococcus pneumoniae with plasmids containing cloned fragments of the pspA structural gene, it has been possible to produce soluble fragments of PspA that are secreted by pneumococci.

In another aspect of the present invention, therefore, there is provided a method of forming an immunoprotective truncated PspA protein, which comprises effecting insertion-duplication mutagenesis of a bacterium with a pspA gene resulting in the coding of a truncated expressible PspA protein, growing the mutated bacterium to effect expression of a truncated PspA protein, and isolating the protein.

The molecular size of the purified truncated PspA protein obtained may be varied by directing the point of insertion, which determines the termination of gene expression, to different points in the pspA gene. For example, an N-terminal fragment of apparent molecular weight of 43 kD, constituting approximately one-half of the native protein, has been found useful.

The truncated segment which is produced by this procedure is capable of eliciting protection in mice from fatal challenge with type 3 S. pneumoniae, demonstrating for the first time that a purified PspA can elicit protection and that this truncated segment of the protein contains protective epitopes of PspA.

Figures 1, 2:
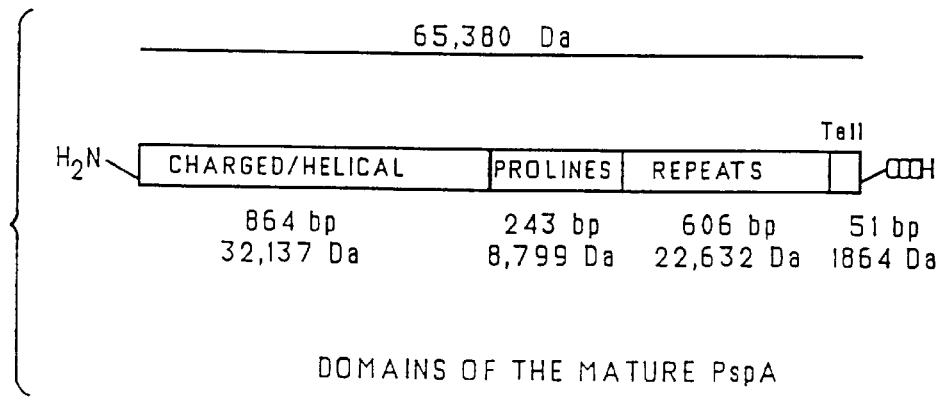
FIG. 1 is a schematic representation of the domains of the mature PspA.
FIG. 2 is the N-terminal amino acid sequence of PspA, (see SEQ ID No. 3) wherein upper case letters denote charged hydrophilic amino acids, lower-case letters designate apolar, hydrophobic residues, and underlined lower case letters denote uncharged, polar, hydrophilic residues.

Amino acid sequence information was obtained on the N-terminal 45 amino acids of the truncated segment of PspA. This sequence is shown in FIG. 2 (SEQ ID No: 3). Predictive secondary structural analysis shows that this sequence has a very strong alpha-helical formation, with no non-helical inserts. About 51% of the segment is composed only of two amino acids, namely lysine, a charged amino acid, and alanine, a non-polar amino acid.

Analysis of this 45-amino acid sequence also reveals that it contains a seven-residue periodicity (see FIG. 2 (SEQ ID No: 3)). In PspA, the periodicity begins with residue 8 and extends throughout the entire sequence, for nearly eleven turns of the helix. Positions "a" and "d" are occupied by apolar amino acids and position "b", "c" and "f" generally contain hydrophilic amino acids. Position "f" is predominantly occupied by lysine. Having regard to these observations, this region of PspA is very likely in an alpha-helical coiled-coil configuration. The deduced amino acid sequence for the whole of the α-helical coiled-coil region is shown in FIG. 5 (SEQ ID No: 4).

Figure 3A:
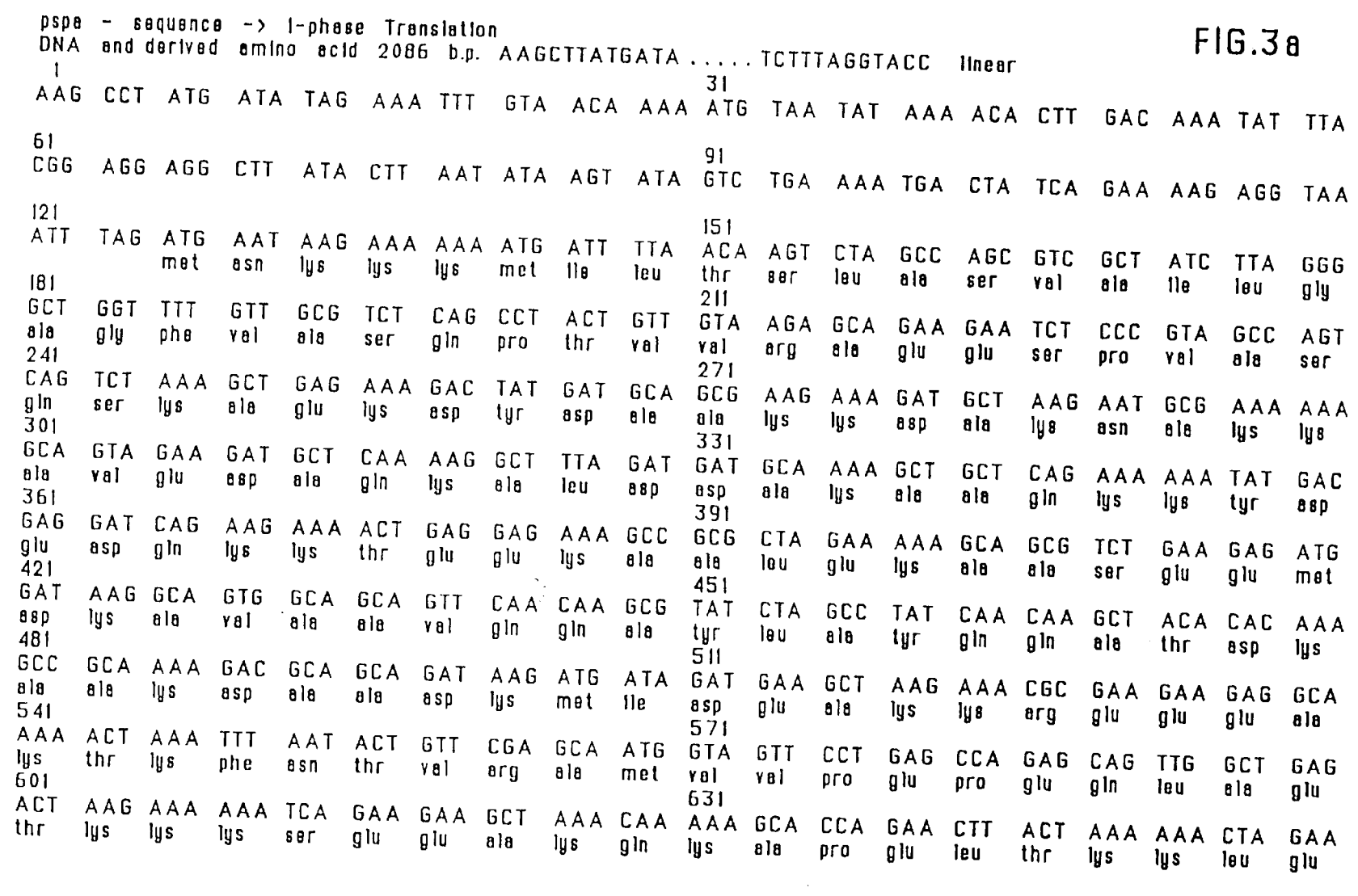
Figure 3B:
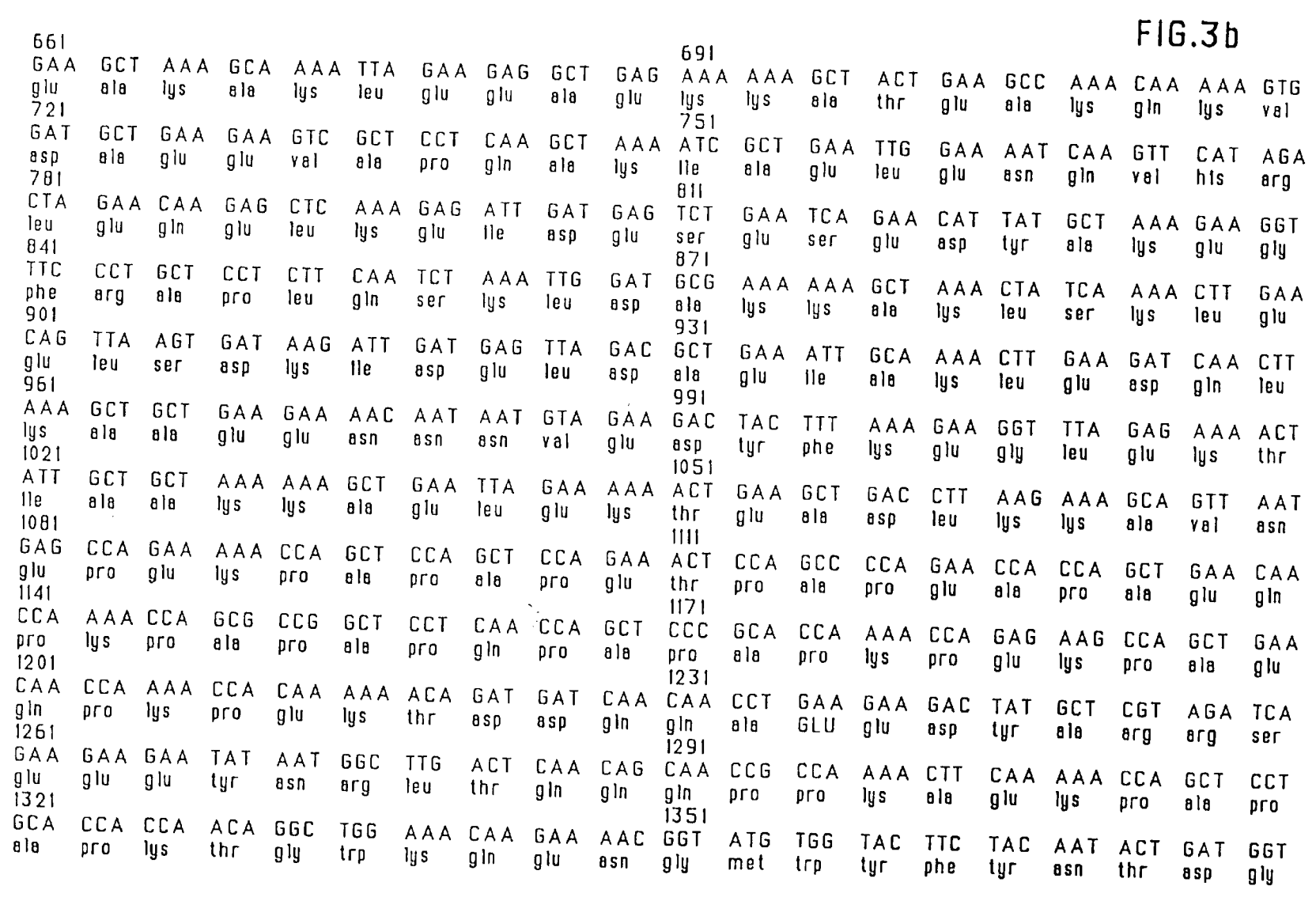

We also have cloned and sequenced the entire coding region of pspA (see FIGS. 3A–C (SEQ ID No: 1)). The deduced amino acid sequence for the PspA protein reveals three distinct regions of the PspA molecule, shown schematically in FIG. 1. Accordingly, a further aspect of the present invention, there is provided a biologically-pure recombinant DNA molecule coding for the PspA protein or portions thereof and having a coding sequence included within set forth in FIG. 3 (SEQ ID No: 1) or having substantial homology thereto.

The DNA sequence of the pspA gene is contained on a HindIII-KpnI fragment that is 2086 base pairs in length. The pspA gene itself represents approximately 1985 base pairs of this fragment, and comprises an initial region containing transcription and translational signals with translation starting at the ATG/met (nucleotide position 127,), followed by a leader sequence extending from the ATG/met (nucleotide position 127,) to GCA/ala (nucleotide position 217). Mature Pspa starts with the glu amino acid at nucleotide position 220 and ends at the translational stop TAA/OCH at nucleotide position 1984. This translational stop codon is followed by transcription termination signals.

The amino terminal of the protein sequence, predicted from the DNA sequence of FIGS. 3A–C (SEQ ID No: 1), contains a 31 amino acid leader sequence and a 45 amino acid sequence identical to the 45 amino acid sequence of the N-terminal of PspA (FIG. 2 (SEQ ID No: 3)). The amino end of the predicted protein sequence is highly charged and α-helical in nature. This region has homology with tropomyosin at the amino acid level (approximately 22% identity and 50% similarity). This homology is due largely to a repeating seven residue periodicity where the first and fourth amino acids are hydrophobic, the intervening amino acids are helix-promoting and the seventh amino acid is charged. This pattern is consistent with that of an α-helical coiled-coil molecule and indicates that the α-helical coil extends through the N-terminal half of the molecule. The amino acid sequence of the whole of the α-helical coil region is shown in FIG. 5 (SEQ ID No: 4).

Following the charged helical region is a proline-rich region in which 23 of 81 amino acids are prolines. Immediately carboxy to the proline-rich region is the first of ten highly homologous twenty amino acid repeats. The only significantly hydrophobic region in the sequenced portion of the molecule begins at the last repeat. This potential membrane-spanning region contains several charged amino acids preceding the translational stop codon.

The insertionally-inactivated mutants of S.pneumoniae lacking the C-terminal anchor regions are capable of growth in chemically-defined medium and secrete the N-terminal portion of the PspA protein into the medium. The N-terminal region of PspA is highly soluble in the culture medium and is much easier to isolate than the entire molecule. Soluble truncated molecules have been produced using insertional duplicational mutagenesis directed by the cloned PspA DNA fragments shown in FIGS. 4A–B. Expression of the same truncated construct (with the pneumococcal promoter) in E.coli results in the same PspA fragment being secreted into the periplasm of E.coli. PspA is readily released from the periplasm by hypotonic lysis.

Truncated PspA is isolated from culture medium of mutant pneumococci in any convenient manner, such as by tangential flow filtration. Ion-exchange chromatography then is performed on an anionic resin to purify the protein. In this procedure, the solution containing PspA is dialyzed to pH6 in 0.02M salt solution and passed over the resin. The PspA is eluted from the resin with a gradient of 0.08 to 2.0M ionic strength and is collected in the fraction between 0.34 and 0.87M ionic strength, depending on the nature of the column used.

The PspA may be further purified by sodium dodecyl sulfate polyacrylamide gel (SDS-PAGE) electrophoresis. The PspA-containing portion of the gel is identified by staining of the gel and PspA is electroeluted from this portion.

The electrophoresis purification is convenient when only small quantities of PspA are being handled. As an alternative, more suited to large-scale production, the protein may be purified by size chromatography in a pH7 phosphate buffer.

Since it is possible to obtain expression of the truncated form of PspA into the culture medium, as opposed to it being trapped within the cell wall and making purification much more complicated, it is possible to isolate other proteins that have been cloned into the truncated pspA gene by making fusion proteins between PspA and other proteins. Such a technique may be employed to enhance the immunogenicity or preserve the immunogenic structural conformation or presentation of the gene product, to permit the fusion protein to be used in immunization, which may be systemic and/or mucosal, against disease.

One example of such a fusion protein is a fusion of the soluble N-terminal region of PspA and the B-subunit of cholera toxin. Fusion proteins also may be formed by chemical attachment of the truncated PspA protein to other proteins.

Another aspect of the present invention, therefore, provides a method for the production of cloned proteins, which comprises fusing a pspA gene coding for a truncated form of PspA protein with the gene coding for another protein to form a fusion protein clone, transforming S.pneumoniae, E.coli or other bacteria with the fusion protein clone, growing the transformed bacterium to effect expression of a fusion protein comprising truncated PspA and the other protein into the culture medium, and isolating the fusion protein.

By using this technique, there can be produced cloned proteins in gram positive bacteria, such as pneumococci, for example, S. pneumoniae, and mycobacteria, for example, Bacille Calmette-Guerin (BCG). This approach overcomes the problems inherent in the production of proteins in gram negative bacteria, such as E. coli, usually used for cloning, in particular the need to purify the recombinant proteins from endotoxin and the toxicity of many gram positive DNA sequences in gram negative organisms.

For the expression of a fusion protein comprising the soluble N-terminal region of PspA and the B-subunit of cholera toxin (CTB), a gene fusion of a pspA gene coding for a truncated form of PspA protein with a ctxB gene coding for the B-subunit of cholera toxin is effected. Following expression of the fusion protein, the PspA and CTB may be cleaved one from another by dilute acid at an asparagine-proline sequence, known to be labile to dilute acid, engineered at the fusion site of the two proteins.

CTB is known to be highly specific for monosinloganglioside ($G_{M1}$). Accordingly, the fusion PspA-CTB protein may be isolated from the culture medium by adsorption to a $G_{M1}$ affinity column, from which the fusion protein subsequently may be eluted at low pH.

The PspA-CTB fusion protein finds considerable utility in solid phase immunoadsorbant assays. By using the fusion protein, it is possible to coat solid supports, such as microtitration plates, with PspA fragments without having first to isolate the PspA fragments. This may be done by adding bacterial extract containing the fusion protein to plates coated with $G_{M1}$. The PspA-CTB fusion protein then binds to $G_{M1}$ through the CTB moiety, thereby coating the solid support with PspA. The resulting coated product then may be used in a solid phase immunoadsorbant assay for the detection of PspA antibody and/or antigen in test samples. Such immunoadsorbant assays constitute an additional aspect of this invention.

The PspA attachment/anchor region, containing the proline-rich region, the repeat region and/or the C-terminus of PspA, also may be employed to effect expression of heterologous proteins in pneumococci, or other gram positive or gram negative bacteria in the which the attachment/anchor region is functional. Generally, expression is effected on bacterial membrane, cell walls or cell surfaces in gram positive bacteria and in the periplasm of gram negative bacteria. An example of such heterologous protein is the B-subunit of cholera toxin.

As mentioned above, the truncated form of PspA provided herein contains the immunoprotective epitopes of the protein and hence is useful in a vaccine against pneumococcal infection. Accordingly, a yet further aspect of the present invention provides a vaccine against pneumococcal infection comprising, as an immunogenically-active component, the purified immunoprotective pneumococcal surface protein provided herein. The PspA protein may be employed as one component of a multicomponent vaccine which is effective in providing protection from a variety of infections.

In addition, gram positive bacteria which have been transformed to express the pspA gene coding for the truncated soluble PspA protein may be employed, in a live-attenuated or killed form, as an immunologically-active component of a vaccine against pneumococcal infection. In the transformed bacterium, such pspA gene may be fused to a gene coding for another protein. Accordingly, an additional aspect of this invention provides a vaccine against pneumococcal infection comprising, as an immunologically-active component, a live-attenuated or killed bacteria containing a gene coding for the truncated form of PspA.

The truncated form of PspA also may be employed in conjugates with normally weakly-immunogenic or non-immunogenic protection-eliciting molecules, such as various polysaccharides, to achieve immunogenic potentiation thereof. An additional aspect of the invention, therefore, provides a vaccine comprising, as an immunogenically-active component, a conjugate of the purified immunoprotective pneumococcal surface protein provided herein and a normally weakly-immunogenic or non-immunogenic protection-eliciting molecule.

Conserved sequences of pspA, particularly those in the proline-rich and/or repeat regions of the gene, may be employed as probes to detect the presence of *pneumococci* of various strains, through detection of pneumococcal DNA, in tissues, body fluids and/or secretions. Similarly, portions of the pspA gene may be used in diagnostic kits for the detection of pneumococcal infections.

In addition, primers made based on conserved sequences of pspA, particularly those in the proline-rich and/or repeat regions, may be used to assay for the presence of *pneumococci* in tissues, body fluids and/or secretions, through amplification of pneumococcal DNA. In this regard, a single primer pair derived from the nucleotide sequence of the pspA gene of *S.pneumoniae* may be employed in an assay using the polymerase chain reaction (PCR) for the specific detection of *Streptococcus pneumoniae*.

Specific amplification has been achieved of a 678 base pair DNA fragment from *S.pneumoniae* strain Rx1. After 30 cycles of amplification, the amplimer was detectable by agarose gel electrophoresis. The fragment was successfully amplified in all 32 strains of *S.pneumoniae* tested. PCR DNA amplification was able to detect less than an estimated 20 ficograms total genomic pneumococcal DNA.

Primers LSM1 and LSM2, having the nucleotide sequences:
LSM1 5'-CCGGATCCAGCTCCTGCACCAAAAC-3' (SEQ ID No: 5)
LSM2 5'-GCGCTGCGACGGCTTAAACCCATTCACCA TTGG-3' (SEQ ID No: 6)
amplified the 678 base pair product from pspA from nucleotides 1312 to 1990 of the Rx1 pspA sequence (FIGS. 3A–C (SEQ ID No: 1)).

The PCR analysis using the primers described herein is performed in accordance with conventional PCR techniques, such as are described in the literature, for example, as described in Arnhem et al at C&EN Special Report, 36, Oct. 1, 1990. For detection purposes, the primer may be labelled or labelled nucleotide triphosphates may be included in the PCR reaction to label the PCR amplification product.

The PCR primers may be prepared by well-known methods, for example, by oligonucleotide synthesis or by fragmentation of a larger nucleotide sequence using suitable restriction enzymes.

The ability to use a single primer capable of detecting a large number of *S.pneumoniae* strains enables a universal PCR detection kit to be provided which is able to diagnose pneumococcal infection in mammals, including humans, independent of the strain which has caused the disease.

STRAINS, PLASMIDS AND PROBES

In the Examples which follow as well as in the accompanying drawings, reference is made to certain plasmids and bacterial strains transformed by such plasmids as well as vector DNA segments, some of which have been deposited with ATCC and all of which are fully described herein. The following Table II provides a summary of such materials.

TABLE II

Figure 7:
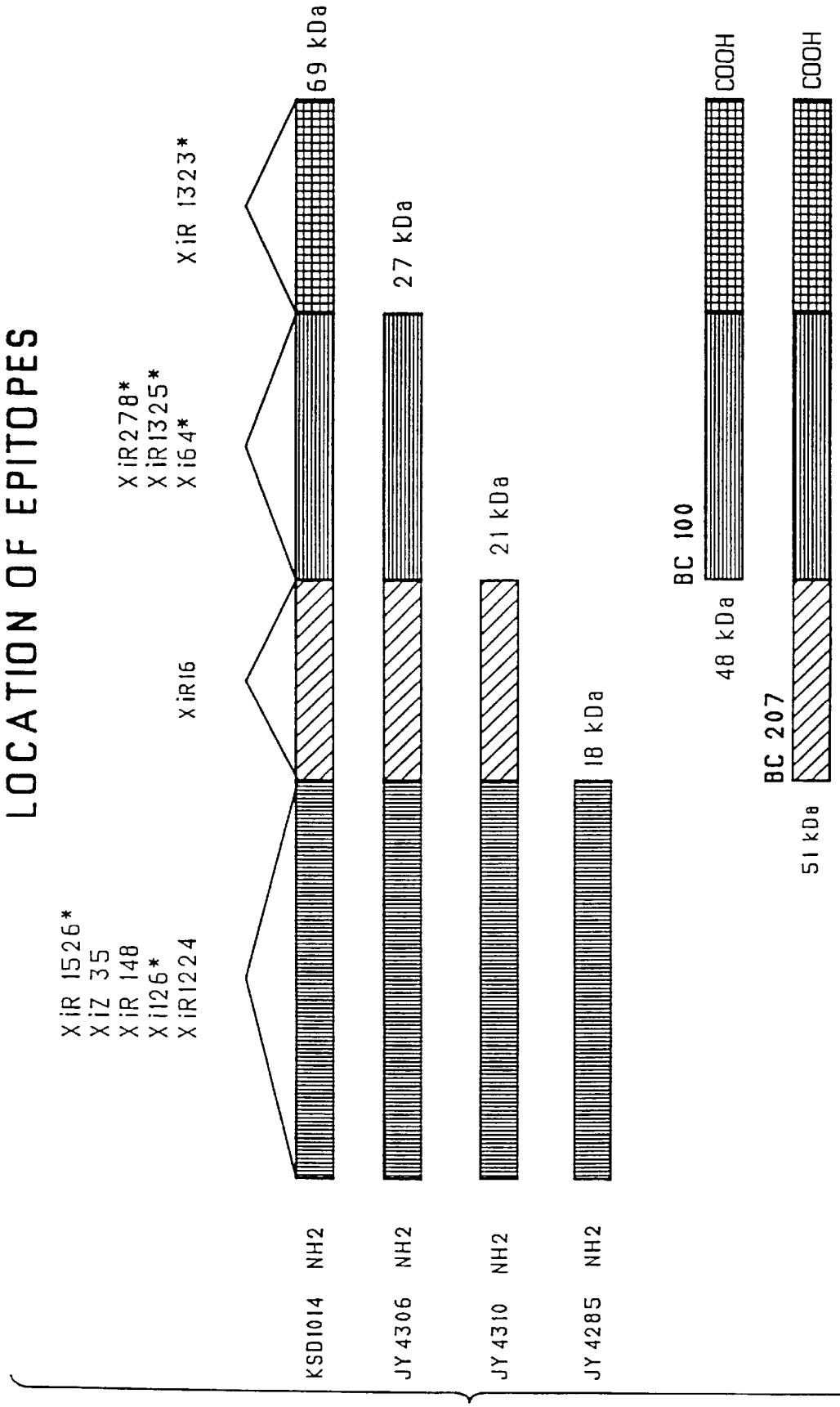
FIG. 7 shows the mapped location of epitopes in the PspA fragments produced by the different pspA gene segments.

| Identification | Type | Description | Deposit | Location |
| --- | --- | --- | --- | --- |
| JY4313 | E. coli strain | PspA DNA | ATCC 68529 | Example 1 |
| JY2008 | S. pneumomiae strain | PspA fragment 43 kDa | ATCC 55143 | Example 1 |
| JY4306 | E. coli strain | PspA fragment 43 kDa | ATCC 68522 | Example 3 |
| JY4310 | | PspA fragment 21 kDa | None | FIG. 7 |
| JY4285 | | PspA fragment 18 kDa | None | FIG. 7 |
| pJY4163 | Plasmid | Expression plasmid used for expression of PspA -CTB fusion protein (29 kDa) | None | Example 6 |
| JY4323 | DNA probe | HindIII-KpaI segment | None | Example 9 |
| JY4306 | DNA probe | HindIII-Dra-I segment | None | Example 9 |
| JY4262 | DNA probe | BclI-Bst-NI segment | None | Example 9 |

EXAMPLES

Example 1

This Example illustrates the preparation and growth of novel strains of *S. pneumoniae*.

The *S. pneumoniae* strain Rx1, which is a non-encapsulated derivative of capsular type 2 strain D39 (National Collection of Type Cultures, 61 Colindale Avenue, London, NW9 SHT, UK under NCTC #7466), was subjected to insertional inactivation (as described in McDaniel et al (III) 1987, Crain et al 1990, Talkington et al 1991, with 10 different cloned fragments of PspA (see FIGS. 4A–B). These fragments have all been obtained from restriction digests of cloned PspA DNA on a plasmid in E.coli strain JY4313 (deposited with the American Type Culture Collection 112301 Parklawn Road, Rockville, Md., 20859on Jan. 31, 1991 under ATCC accession number 68529). This insertional duplication mutagenesis (see FIGS. 4A–B) results in the termination of gene expression near the 3' end of the cloned fragment.

One of the resultant strains, JY2008 (deposited with the American Type Culture Collection on Jan. 24, 1991 under accession number 55143), which was produced by a fragment of DNA encoded in pKSD300 (McDaniel et al (III) 1987), produces a PspA fragment of 27 kDa (apparent molecular weight 43 kDa). This fragment is approximately 40% the size of the native 65 kDa (84 kDa apparent size) protein.

The expected molecular size is based on the deduced amino acid sequence and the apparent molecular size is based on migration in SDS-PAGE. The difference between expected and apparent molecular size is due to the conformation of the PspA fragment.

The proline and repeats/anchor regions (see FIG. 1) were deleted and the resulting protein was unable to attach to cell due to their absence. The unattached protein then may be isolated from culture supernatants, as described below.

By directing the insertion to different points in the pspA gene, different lengths of truncated, non-attached PspA protein derivatives can be produced, as seen in FIG. 7.

The pneumococcal strain JY2008 was grown in 6 liters of a chemically defined medium (see Inf. Imm. 27:444) supplemented with 0.10% choline chloride, 0.075% L-cysteine hydrochloride and 0.25% $NaHCO_3$. The supernatant fluid of the mid-log phase culture of JY2008 was harvested using a 0.22 μm membrane tangential flow filter and concentrated 60 fold.

Introduction of the plasmid pKSD300 into the unmodified D39 strain similarly yielded the 43 kD truncated PspA protein. Introduction of the plasmid pKSD300 into the type 3 *S.pneumoniae* strain WU2 (PspA protein approximately 92 kD) yielded, upon growth of the organism, a non-attached truncated PspA protein of approximately 46 kD molecule size.

Example 2

This Example illustrates the purification of PspA.

The concentrated supernatant fluid, produced as described in Example 1, was washed in 0.1M PBS, pH 7.2, and ultracentrifuged at 196,000 xg. The supernatant fluid was diluted 1:5 in 20 mM L-histidine buffer-NaCl, the pH adjusted to 6.0 and the injected into a DEAE-fibered Isonet-D2 an ion exchange column.

A stepwise NaCl gradient from 80 mM to 2M was applied to the column and PspA-containing fractions (0.32 to 0.64M ionic strength) were pooled and separated on an SDS-polyacrylamide gel. The proteins on a representative section of the gel were stained with Comassie Blue R-250 to identify PspA. The fraction containing PspA was excised from the remainder of the SDS-gel and electroeluted from the excised gel. The eluted protein was precipitated in a 50:50 methanol:acetone solvent and resuspended in PBS. Purity of product was confirmed by silver staining and Western Immunoblotting with mAb Xi126 (IgG 2b, k, see McDaniel et al (I), supra).

Example 3

This Example illustrates the isolation of PspA from the periplasmic space of *Escherichia coli*.

Isolation from the periplasmic space of *E. coli* was accomplished by standard techniques. *E. coli* strain JY4306 (which produces the 43 kDa N-terminal fragment of PspA, the amino acid sequence of which is shown in FIGS. 3A–C (SEQ ID No: 1). This strain was deposited with ATCC on Jan. 31, 1991 under accession number 68522) was washed in buffered saline, incubated in 20% sucrose, 10 mM EDTA, 25 mM Tris pH 7.7 for 10 minutes at 0° C. The cells then were spun at 400 xg for 10 minutes at 0° C. All supernatant was removed from the pellet and the pellet was resuspended rapidly in about 100 volumes of 4° C. water. After 10 minutes the suspension was centrifuged at 4,000 xg for 10 minutes at 4° C. The pellet was discarded and the supernatant, which contained the PspA was saved. Concentration of the supernatant was by standard procedures such as concentration against solid sucrose or ultrafiltration. Purification of the protein isolated from *E. coli* proceeded by the same chromatography techniques used for the isolated of the 43 kDa (truncated) PspA from the media of growing *pneumococci*.

Example 4

This Example illustrates the immunogenic properties of the PspA protein.

Sixteen 7-week old CBA/N mice carrying the Xid mutation (Jackson Laboratories, Bar Harbor, Me.) were bled via the periorbital sinus to establish pre-exposure levels of antibody to PspA. Purified PspA, prepared as described in Example 2, was emulsified in complete Freund's adjuvant and injected subcutaneously into the inguinal and axillary regions, delivering approximately 5 μg of protein per mouse. Fourteen days later, the mice were injected intraperitoneally with 5 μg of PspA, prepared as described in Example 2. Control mice were immunized via the same routes with sterile SDS buffer. Seven days after the last immunization, all mice were bled via the periorbital sinus and were challenged intravenously with 300 CFU of the type 3 strain WU2, grown as described in Example 1.

Preimmunization and prechallenge sera were analyzed by Western immunoblots to establish baseline and postimmunization response to the truncated protein. The PspA of strain WU2 was electrophoresed and transferred to nitrocellulose membranes. The membranes were separated into strips and probed with the appropriate mouse antisera at a 1:50 dilution for 2 hours, incubated with biotinylated goat anti-mouse immunoglobulin for 1 hr, washed and incubated with Strepavidin-conjugated phosphatase. The membranes were developed with 5-bromo4-chloro-3-indoyl phosphate toludine salt with 0.01% into blue tetrazolium.

Of the eight CBA/N mice immunized with the purified fragment of PspA, all were still alive 14 days after challenge with strain WU2 and none showed any signs of illness following challenge. Of the eight mice immunized with buffer controls, six were dead by two days post challenge, while the two remaining control mice appeared very sick, with ruffled fur, arched back and decreased movement, two to three days following challenge but survived. Chi-square analysis indicated that there was a significant difference ($P<0.003$) in survival between the immunized and control groups.

Preimmunization and prechallenge sera were analyzed by Western immunoblotting. None of the preimmunization sera contained antibody to truncated PspA. Postimmunization sera from eight of eight mice contained detectable antibodies to PspA, and six mice had very strong anti-PspA reactions. When the challenge strain WU2 was probed with the antisera, all the immunized mice had antibodies that were highly cross-reactive with the WU2 PspA epitopes. No control mice developed antibodies to PspA.

The immunization data is summarized in the following Table III:

TABLE III

| Immunogen | Detection of Antibody to PspA | Alive at 2 days post challenge | Alive at 14 days post challenge |
|---|---|---|---|
| Isolated PspA (Example 2) | 8/8 | 8/8 | 8/8 |
| Sterile SDS (control) | 0/8 | 2/8 | 2/8 |

As may be seen from the data in Table III, immunization with two 5 μg doses of the purified PspA molecule elicited protection against fatal infection of CBA/N mice and elicited antibodies reactive with the PspA of the challenge strain.

Example 5

This Example illustrates sequencing of the PspA protein.

Purified PspA, prepared as described in Example 2, was electrophoresed through 9% resolving gels containing recrystallized SDS with the Laemmli buffer system (Nature 227:680). The gels were soaked twice in a 10 mM 3-(cyclohexylamino)-1-propanesulfonic acid, pH 11.0, containing 10% methanol for 10 minutes. A polyvinylidene difluoride membrane (PVDF) was wetted completely for several seconds in 100% methanol, then washed in CAPS buffer for 10 min. PspA was electrotransferred to the PVDF membrane in CAPS buffer at 0.5 A for 1 hr. After transfer, the membrane was washed two times in deionized water for 5 min, and stained with 0.1% Coomassie Blue R-250 in 50% methanol for 20 minutes. The section of the membrane containing PspA was excised and destained in 40% methanol and 10% acetic acid for 5 min. The membrane was cut into small segments and stored in sterile Eppendorf tubes until sequencing.

The isolated PspA was sequenced directly from the PVDF membranes. FIG. 2 depicts the N-terminal 45 residue amino acid sequence and FIG. 5 depicts the amino acid sequence for the whole alpha-helical region. The DNA sequence of the whole pspA gene and the deduced amino acid sequence for the PspA protein are shown in FIGS. 3A–C (SEQ ID No: 1).

Example 6

This Example illustrates the use of the pspA 5'-sequence and/or the PspA N-terminal region to serve as an expression and leader sequence for expressing and/or excreting/secreting heterologous proteins from *S.pneumoniae* and *E.coli*. In this Example, there is described the expression of the N-terminal of the PspA protein fused to the B-subunit of cholera toxin (CTB) through a genetic fusion and the excretion of the fused protein from *pneumococci* and its secretion into the periplasmic space of *E.coli*.

A fusion protein consisting of CTB and the N-terminal half of PspA was constructed and expressed in *E.coli*. The HindIII/DraI pspA gene fragment used contained all the pspA transcription and translation initiation signals and the PspA signal peptide leader sequence for transport across the cell membrane. The mature PspA encoded by this fragment is predicted to be a product of 29 kDa (observed molecular weight of 42 kDa), encompassing more than 90% of the α-helical coiled-coil domain. The CTB fragment used lacked transcription and translation initiation signals. Expression from pspA promoter through pspA and then in-frame translational readthrough into the CTB-encoding gene ctxB resulted in production of a 12 kDa CTB product fused to the upstream PspA product. The PspA-CTB fusion protein was stably expressed in both high and low copy number plasmids (pUC18, more than 100 copies/cell; pJY4163, about 15 to 30 copies/cell) in *E.coli*.

The fusion products were of the expected size (about 54 kDa) and reacted with antibody to both PspA and CTB. That the CTB product retained its functionality was demonstrated by the ability of the fusion protein to bind ganglioside $G_{M1}$, a property of CTB.

The high level of expression of the fusion product apparently resulted in a reduced rate of processing and/or conformational changes that prevented the protein from being completely transported to the periplasm. However, in the lower copy number construct, about 60% of the fusion protein was localized in the periplasm, where large quantities were readily released from *E. coli* by osmotic shock.

In addition to expression in *E.coli,* the fusion protein also was expressed in *S.pneumoniae* by transformation of the low copy number construct into the avirulent *S.pneumoniae* Rx1 to generate an insertion-duplication mutant. In this way, the gene encoding the fusion protein was integrated into the *S.pneumoniae* chromosome, from which it was stably expressed. As in the case of Example 1, the truncated PspA molecule lacking the attachment/anchor region, this time in the form of the PspA-CTB fusion protein, was excreted into the culture supernatant. The fusion protein product was of the expected molecular size (54 kDa), reacted with antibody to PspA and CTB, and bound $G_{M1}$.

Example 7

This Example illustrates the use of PspA attachment or anchor region to permit expression of heterologous proteins on the surface of *S.pneumoniae* or other bacteria in which the attachment/anchor sequence is functional in particular the expression of a PspA-CTB (cholera toxin B subunit) fusion expressed on the surface of *pneumococci*.

The N-terminal encoding region of PspA, including its transcription and translation initiation signals and its signal peptide leader sequence, is linked via a translationally in-frame genetic fusion to the CTB-encoding ctxB fragment that lacks transcription and translation initiation and termination signals. This sequence is followed in-frame by the PspA attachment/anchor domain, including part or all of the proline, repeat and C-terminal domains. The resulting fusion protein is directed to the outside of the cell via the PspA leader sequence, which is cleaned following transport across the membrane, and then attached to cell by the PspA attachment/anchor sequence. The heterologous protein, located between the two PspA fragments is expressed on the outside surface of the membrane and, in *S. Pneumoniae,* on the surface of the cell.

Example 8

This Example illustrates the expression of truncated and full length PspA by the *Mycobacterium tuberculosis* strain Bacille Calmette-Guerin (BCG).

BCG was chromosomally modified to incorporate the pspA gene coding for the truncated PspA protein. The 43 kDa truncated PspA protein was expressed from the modified BCG to approximately 15% of total BCG protein. This result was achieved with an expression vector construct carrying the pspA gene segment encoding the 43 kDa region without its 5'-secretion signal. Expression was only about 1% of BCG protein when the PspA or mycobacterial signal sequences were included. In either case, a significant portion of the expressed PspA was excreted into the medium. Expression of the 43 kDa PspA protein in a fusion with the mycobacterial lipoprotein signal sequence resulted in the expression of the recombinant PspA in the membrane fraction of BCG.

This latter result suggested that the fusion of the lipoprotein signal sequence resulted in acylation of the recombinant PspA. Fluorescent activated cell sorting with fluorochrome-conjugated monoclonal antibodies to PspA demonstrated expression of PspA on the surface of these bacteria.

Example 9

This Example illustrates the close homology of portions of the pspA gene among different strains of *pneumococci* and the potential that such homology may be useful for molecular (DNA) approaches to detect *pneumococci* in tissues, body fluids and/or secretions and to identify *pneumococci* grown from patient samples.

Three DNA probes were employed, namely full length pspA, JY4323 (N-terminal HindIII to C-terminal KpnI), the N-terminal half of pspA, JY4306 (N-terminal HindIII to DraI at position 996 (see FIGS. 3A and C (SEQ ID No: 1)) and most of the proline and repeat regions, JY4262 (BclI at position 1221 to BstNI at position 1832). Under stringency conditions requiring 95% identity, probes JY4323 and JY4262 reacted with cells of over 200 independent isolates of *S.pneumoniae* by Southern blot.

When the chromosomal DNA was cut with HindIII, there generally was observed that each of these probes detected two discrete bands whose exact size was dependent on the strain examined. In Rx1 *pneumococci*, the two bands were 4.0 and 9.1 kb. The 4.0 kb band corresponded to pspA and was altered or absent in pspA mutants. The other band shares some homology with the coding regions for both the N-terminal and C-terminal halves of PspA but is not affected by pspA mutations. The JY4323 and JY4262 probes failed to react with another gram positive bacterium, *Streptococcus pyogenes,* and a gram negative bacterium, *Salmonella typhimurium.* The N-terminal probe, JY4306, recognized about one-third of the strains of *pneumococci* tested.

These results indicate that a sequence included in the proline/repeat region is shared by all strains of *pneumococci* and apparently not by other bacterial species. Sequences in the N-terminal half of the molecule appear to be more variable.

Example 10

This Example illustrates the detection and determination of the location of epitopes in the α-helical N-terminal region of PspA.

Monoclonal antibodies protective against pneumococcal infection in a mouse model, denoted by an asterisk in FIGS. 5, 6 and 7, were used to determine the location of epitopes for each antibody in the α-helical N-terminal region of PspA. The sites were mapped to fragments of PspA. The results are illustrated in FIGS. 5 to 7, with FIG. 5 showing the deduced amino acid sequence for the N-terminal region of PspA and the general location of epitopes recognized by monoclonal antibodies, FIG. 6 showing antibody reactivity with PspA fragments produced by various pspA gene segments, and FIG. 7 showing the mapped location of epitopes in the PspA fragments produced by the different pspA gene segments.

Numbers 138, 193 and 261 in FIG. 5 indicate break positions in the PspA fragments used to map the location of epitopes detected by monoclonal antibodies Xi1526, Xi126, XiR35, XiR38, XiR1224, XiR16, Xi64, XiR278, Xi1325 and Xi1323. The asterisk (*) after some of the antibodies denotes those which are able to protect against fatal pneumococcal infection with strain WU2 *pneumococci.*

In addition, the vertical lines to the right of the Figure indicate those areas predicted to have coiled-coil α-helical structure. The divisions to the left of the Figure indicate the mapped location of the epitopes for each antibody.

SUMMARY OF DISCLOSURE

In summary of this disclosure, the present invention relates to a truncated PspA molecule capable of eliciting an immunoprotective response and hence containing the protective epitopes of PspA protein. Modifications are possible within the scope of this invention.

SEQUENCE LISTINGS

Submitted with this application are Sequence Listings, identified as follows:

(a) SEQ ID No: 1 shows the nucleotide sequence and derived amino acid sequence for the HindIII-KpnI fragment containing the complete pspA gene, as shown in FIG. 3.

(b) SEQ ID No: 2 shows the derived amino acid sequence for the PspA protein, as shown in FIG. 3.

(c) SEQ ID No: 3 shows the N-terminal amino acid sequence of PspA, as shown in FIG. 2.

(d) SEQ ID No: 4 shows the derived amino acid sequence for the N-terminal region of PspA as shown in FIG. 5.

(e) SEQ ID No: 5 shows the nucleotide sequence for primer LSM1.

(f) SEQ ID No: 6 shows the nucleotide sequence for primer LSM2.

What we claim is:

1. A solid phase immunoabsorbant assay for the detection of PspA antibody or PspA antigen, wherein, the improvement comprises a coating of a truncated form of a whole pneumococcal surface protein (PspA) on a solid phase substrate, wherein said truncated form of the PspA protein is fused to the B-subunit of cholera toxin (CTB), which is bound to monosinloganglioside ($G_{M1}$) coating said solid substrate, wherein said truncated form of the PspA contains the immunoprotective epitopes of the whole PspA, up to 90% of the whole PspA, and does not contain the cell membrane anchor region wherein said whole PspA comprises the sequence as set forth in FIG. 3 (SEQ ID No. 2).

2. The assay of claim 1, wherein said truncated form of the PspA protein contains about 50% of the whole PspA protein and does not contain the cell membrane anchor region, the repeat region or the proline region.

3. The assay of claim 1, wherein said truncated form of the PspA protein comprises at least the N-terminal, protective epitope containing region of the whole PspA protein, said whole PspA protein having the domains which comprise the sequence as set forth in FIG. 3 (SEQ ID No. 2).

4. The assay of claim 1, wherein said truncated form of the PspA protein comprises the 43 kD (apparent molecular size) N-terminal region of an 84 kD whole PspA protein.

* * * * *